United States Patent [19]
Balassa

[11] 3,966,908
[45] June 29, 1976

[54] METHOD OF TREATING DEGENERATIVE JOINT AFFLICTIONS

[75] Inventor: Leslie L. Balassa, Blooming Grove, N.Y.

[73] Assignee: Lescarden Ltd., Goshen, N.Y.

[22] Filed: July 10, 1975

[21] Appl. No.: 594,697

Related U.S. Application Data

[63] Continuation of Ser. No. 420,257, Nov. 29, 1973, abandoned.

[52] U.S. Cl. ................................................. 424/95
[51] Int. Cl.² .......................................... A61K 35/32
[58] Field of Search ..................................... 424/95

[56] References Cited
UNITED STATES PATENTS

| | | | |
|---|---|---|---|
| 3,318,774 | 5/1967 | Dingwall et al. | 424/95 |
| 3,400,199 | 9/1968 | Balassa | 424/95 |
| 3,458,397 | 7/1969 | Myers et al. | 424/95 X |
| 3,476,855 | 11/1969 | Balassa | 424/95 |
| 3,478,146 | 11/1969 | Balassa | 424/95 |
| 3,551,560 | 12/1970 | Thiele | 424/95 |
| 3,703,575 | 11/1972 | Thiele | 424/95 X |
| 3,772,432 | 11/1973 | Balassa | 424/95 |

OTHER PUBLICATIONS

Beyerl, K. Biol. Abst. 47 No. 12355 (1966) of Med. Welt. 14:704–706 (1965), "The Treatment of Arthrosis with a Cartilage-Bone Marrow Extract Arumalon".

Adler et al., Acta. Rheum. Scand. 16:6–11 (1970), A Double Blind Trial with Cartilage-Bone Marrow Extract in Degenerative Gonarthrosis.

Dixon et al., Ann. Rheum. Dis. 29:193–194, Mar. 1970, A Double Blind Controlled Trial of Rumalon in the Treatment of Painful Osteoarthritis of the Hip.

Wagenhauser et al., Schweiz, Med. Woch. 98:904–907, June 19, 1968, The Treatment of Arthroses with Cartilage-Bone Marrow Extract.

Pilz Med. Klinik. (Munich), 61:1000–1001, July 8, 1966, Cartilage-Bone Marrow Extract for Treatment of Arthroses of the Large Joints.

*Primary Examiner*—Shep K. Rose
*Attorney, Agent, or Firm*—Darby & Darby

[57] ABSTRACT

A method for treating degenerative afflictions of the joints is described which comprises administering to a mammal suffering from a degenerative joint affliction an effective amount of a produce derived from granulated animal cartilage.

4 Claims, No Drawings

METHOD OF TREATING DEGENERATIVE JOINT AFFLICTIONS

This is a continuation of application Ser. No. 420,257, filed Nov. 29, 1973, now abandoned.

This invention relates to a method of treating degenerative joint diseases in mammals. More specifically, the invention relates to a method of treating osteoarthritis in humans.

The term degenerative joint diseases is applied to a heterogeneous group of diseases, characterized by the appearance of fissures and cracks in the articular cartilage, sclerosis of the subchondral bone, and hypertrophy of the cartilage located at the margin of the affected joint. In most cases, some degree of synovial inflammation is also present.

Osteoarthritis is the most common degenerative joint disease known to man and afflicts an estimated ten million people to a clinically significant degree in the United States alone. More women than men are affected and the incidence of the disease usually increases with the age of the patient. The pathology of osteoarthritis is characterized by destruction of hyaline cartilage and bony eburnation accompanied by the formation of bony spurs (or osteophytes) at the margins of the affected joints. The principal symptoms experienced by osteoarthritic patients are pain in and around the affected joints and a lessening of joint mobility. In advanced cases the joints become knobby due to bone deformities.

There is no known cure for osteoarthritis and the objective of treatment is to alleviate pain and promote increased joint mobility. The medicines currently available to treat osteoarthritis are aspirin (or sodium salicylate) and 1-(P-chlorobenzoyl)-5-methoxy-2-methyl indole-3-acetic acid. In both cases, however, the administration of the drug provides only temporary relief lasting at best for a day or so. Intra articular injection of corticosteroids is temporarily helpful in alleviating synovial inflammation on a local basis, however the effect is localized in the area of the joint which has been injected, and lasts for five to ten days at best. The prolonged administration of corticosteroid medications is hazardous since it can permanently affect the function of the pituitary and adrenal glands. The continuous administration of aspirin is contra indicated in many individuals especially those with abnormal heart or liver conditions. The side effects of the indole acetic acid derivative (e.g., headaches, dizziness and gastrointestinal disturbances) are intolerable to many patients and restrict the use of the drug to obtain symptomatic relief. In addition, the aspirin and indole acetic acid medicines must be administered via the oral route. Oral administration has its drawbacks particularly in the case of elderly patients who may not be able to adhere to the required dosage schedule.

It has now been unexpectedly discovered that degenerative joint afflictions, and specifically osteoarthritis, can be treated by the use of cartilage powder, preferably in the form of an isotonic sterile extract, such cartilage powder having been previously described in U.S. Pat. Nos. 3,400,199, 3,476,855, 3,478,146, and 3,772,432.

In addition, it was found that cartilage powder can be used to treat many non-specific inflammations of the peripheral joints that result in the disablement and eventual destruction of articular and periarticular structures and which are generally denominated as rheumatoid arthritis.

Accordingly, one aspect of the present invention is to provide a method of treating degenerative joint afflictions in humans. Another aspect of the present invention provides for the treatment of osteoarthritis in a patient by administering an effective quantity of a medicine based on cartilage powder.

Still another aspect of the present invention is to provide a method of treating degenerative joint afflictions by the subcutaneous administration of an aqueous extract of cartilage.

These and other aspects of the present invention will become apparent from a consideration of the following description.

As used throughout the specification "cartilage product" means cartilage powder and/or cartilage extract (either solid or liquid) which is derived from granulated cartilage.

The cartilage products used in the compositions of the present invention are known in the art and have been described in U.S. Pat. Nos. 3,400,199, 3,476,855, 3,478,146 and 3,772,432, the disclosures of which are incorporated herein by reference. The cartilage powder is preferably derived from young cartilage, i.e., from young animals or young or newly regenerated cartilage from older animals as reptiles or from species such as fish or shark in which the cartilage remains young eternally. Where age is the criteria for defining "young" the cartilage is preferably derived from animals not over six months old. However, cartilage powder derived from the cartilage of older animals may also be employed but it is not as effective.

The cartilage may be prepared by any suitable means to result in a product which is essentially pure cartilage substantially free from adhering tissue which may have been removed by acid-pepsin or other suitable enzyme treatment, with or without mechanical assistance or otherwise.

The cartilage powder materials used in accordance with the present invention is preferably pulverized to an average particle size of less than about 150 microns, and preferably less than 70 microns. The cartilage powder may be pulverized by any number of techniques including ball milling, hammer milling in an inert atmosphere, pebble milling and fluid energy mill grinding. The granulated cartilage materials may be employed in the preparation of cartilage products including ointment preparations for topical applications and aqueous extracts for administration by injection.

The cartilage extracts are obtained by the use of aqueous extracting agents which dissolve the active components of the cartilage powder. The extract is therefore a product from which a substantial portion of the non-active components have been removed and hence has a higher concentration of activity per unit dose. Examples of suitable extraction aids include ammonia or ammonium carbonate, or such materials which if remaining in the extract would cause no harm. Dialysis may be employed to remove undesired salts or other dialyzable material which may be present. Other extraction aids are urea, sodium citrate, disodium phosphate, trisodium phosphate, sodium formate, sodium chloride and similar compounds or mixtures of them.

The cartilage product preferably used in the treatment of degenerative joint afflictions and osteoarthritis in particular is in the form of an extract with isotonic saline solution. The isotonic saline cartilage extract is prepared into an injectable dosage form by dilution with sterile water to yield a sterile iso-osmolar solution. Determination of the iso-osmolar point can be made for example by using a freezing point osmometer in well-known laboratory procedures which exist for this purpose. The liquid used to extract the cartilage powder for preparation of an injectable dosage unit for treatment of osteoarthritis is preferably isotonic saline solution containing 0.9% NaCl (USP injectable saline).

The cartilage powder or extract may also be suspended in oils such as tung oil, corn oil, olive oil, or linseed oil. The oil dispersions may be emulsified in water, forming oil in water-type emulsions, or conversely, water may be emulsified in the oil dispersions forming water in oil emulsions.

The cartilage powder may also be prepared in the form of a cream or ointment by admixing with a suitable base such as anhydrous propylene glycol. In this manner it is possible to prepare the product in the form of an ointment, salve or salve base incorporating the extract of the present invention.

The injectable cartilage extracts contain from about 1 to about 10 percent and preferably about 6 percent cartilage material and have a pH of about 6.0. In most instances, the sterile extract to be used for injection contains a preservative such as methyl, and/or propyl paraben and is light brown translucent liquid, that is slightly viscous at 20°C and a gel at 0°C. The cartilage extract may be sterilized by autoclaving for 90 minutes at 15 lbs pressure at 121°C with all of its additives, if any, as the final step in the preparation of the sterile iso-osmolar injectable dosage form. Immediately prior to injection, the solution can be diluted 1:10 with 1% lidocaine (or equivalent local anesthetic) to alleviate discomfort.

For treatment of degenerative joint afflictions and osteoarthritis in particular, the sterile cartilage extract is administered subcutaneously in areas of the body possessing a readily distensible subcutaneous space (e.g., the back, anterior thorax, abodomen and anterior thighs). The drug need not be introduced directly at the site or in the location of the affected joint(s) and may be administered at a remote site. The treatment regimen involves introduction of a total dose of between about 75 and 1000 cc's of the extract over a period of about two to eight weeks and preferably about one month. The total dose will generally be between about 450 and 750 cc's and in most individuals will average about 500 cc's. Administration is carried out by subcutaneously injecting from about 10 to about 50 cc and preferably about 25 cc of the sterile cartilage extract into each of several subcutaneous sites or depots. Preferably a total of about 100 cc is injected at one time although smaller amounts can be administered at more frequent intervals in the interest of patient comfort. The injection speed is slow for the same reason. Treatments are administered every second or third day until the total effective dosage has been reached.

A typical patient with clinically significant osteoarthritis required a total dose of about 500 cc of the sterile cartilage extract although the average dose at which an individual patient first noticed some relief was about 175 cc. Each depot should contain not less than about 10 cc nor more than about 50 cc of the sterile cartilage extract. In most cases a subcutaneous depot containing about 50 cc of a sterile extract has been found to give good results.

To minimize the discomfort of a subject due to buildup of the subcutaneous depots, the iso-osmolar solution preferably contains about 10% by weight of lidocaine or a similar material having localized anesthetic action. Between about 75 and about 100 cc of the sterile extract is preferably administered in a single treatment in the interest of alleviating any discomfort that may be caused by the presence of the cartilage depots. Usually between about 4 and about 12 hours is required for the aqueous solution located in each depot to be absorbed into the tissues of the body and eventually into the bloodstream thereby dissipating the stored cartilage deposit.

The following examples are illustrative of cartilage powders and cartilage extracts useful for preparing cartilage products having applications in the treatment of degenerative joint afflictions:

EXAMPLE I

Cartilage Pebble Mill-ground

The tracheas of healthy adult beef cattle were removed within 30 to 60 minutes after the animals were slaughtered. The tracheas were then either processed immediately with an acid-pepsin solution or they were frozen to preserve them, in which case the acid-pepsin digestion may be deferred. The tracheas either fresh or previously frozen were then digested for about six hours at 50°C. in an aqueous solution containing 0.6% acetic acid (U.S.P. glacial) and 0.3% pepsin (N.F. IX grade, 3500 activity). After digestion the tracheal cartilage was removed from the acid-pepsin solution, washed first with water of about 70°C. and then with water of about 25°C. until the effluent wash water showed no trace of pepsin or acetic acid. The cartilage was dried in vacuum (20 mm. mercury) and 80°C. The dried cartilage was defatted by extracting it with a solvent, such as hexane. It was then granulated.

The granulated purified cartilage was ground to a fine powder in a laboratory four-quart size porcelain jar mill, loaded with one-inch size (average) flint pebbles in a weight ratio of 1 cartilage to 2 pebbles. Dry Ice ($CO_2$) was then put on top of the mill charge and the mill was kept open for 5 minutes to allow the $CO_2$ to displace the air in the mill. The lid of the mill was then clamped on tight and the mill rotated as is customary in the performance of the grinding operation. The grinding was carried out at about $-20°C$. for 96 hours. The ground cartilage was screened through a 325 mesh nylon screen, thereby confining the active cartilage powder to particles less than about 40 microns in size, and having average or majority particle size between about 5 and 10 microns.

EXAMPLE II

Cartilage obtained from the tracheas of a one month old calf was obtained by the same procedure as described in Example I and the resulting cartilage was ground to an average particle size of about 40 microns.

Cartilage powder may also be obtained from cartilage sources such as pigs, lambs, goats, skeleton of sharks, rodents, rib cage of crocodiles, birds, fish, etc. Reptile cartilage is particularly desirable in view of the ability of reptiles to regenerate their tissues and even their limbs. More details on the obtaining of cartilage powder from these and other sources will be found in U.S. Pat. No. 3,400,199.

EXAMPLE III

Liquid cartilage extracts were prepared as follows:

The cartilage obtained from a one day old calf was acid-pepsin digested as in Example I, granulated, and then without drying was suspended in the extracting liquid, isotonic saline solution, and then transferred into a pebble mill which was charged to 50% of its volume with flint pebbles of average size, one inch diameter. The ratio of the cartilage to extracting liquid was kept to 25:75. The liquid suspension was charged into the mill in a quantity just sufficient to fill the voids of the pebbles with the top of the pebbles barely covered by the liquid. The air was then purged from the mill with nitrogen and the mill closed. The mill was allowed to run for 6 hours at between 3°C. and 4°C. which resulted in a medium fine grinding of the cartilage and in the simultaneous extraction of the active wound-healing agent from the cartilage.

At the end of the 6-hour cycle, the mill was emptied, the fluid paste strained free of the pebbles, the fluid transferred into a centrifuge operated at 6000 r.p.m. and at a temperature of between 3°C. After one-half hour the centrifuge was stopped and the supernatant liquid strained through a 400 mesh nylon screen. If the strained extract was cloudy, it was returned to the centrifuge and the centrifuging repeated until a clear slightly opalescent extract was obtained.

The extracts were stored at 40°C. preserved with 1:10,000 sodium ethyl mercuric thiosalicylate.

The following extracts were thus prepared:

|   | Cartilage Source | Extracting Liquid | Total Solids of Clear Extract, By Weight, Percent |
|---|---|---|---|
| a | Bovine tracheal | Distilled water | 1.3 |
| b | " | Isotonic saline sol. | 5.2 |
| c | " | Ammonia (28%) 1% in water | 6.5 |
| d | " | 2% urea in water | 9.6 |
| e | " | 1% ammonium carbonate in water | 6.4 |
| f | " | 1% disodium phosphate in water | 6.6 |
| g | " | 3% ammonium carbonate in water | 7.2 |
| h | " | 1% trisodium phosphate in water | 7.6 |
| i | " | 1% sodium citrate in water | 7.0 |
| j | " | 3% sodium citrate in water | 9.2 |
| k | " | 1% sodium formate in water | 8.2 |
| l | Piglet 1 day old | Isotonic saline solution | 6.4 |
| m | " | 1% ammonia (28%) in water | 7.1 |
| n | " | 3% ammonium carbonate in water | 8.1 |
| o | " | 3% sodium citrate in water | 10.0 |
| p | Calf one day old | Isotonic saline solution | 6.2 |
| q | " | 1% ammonia (28%) in water | 7.3 |

Note: The isotonic saline solution was prepared with distilled water and contained 0.9% NaCl.

In addition to pebble mill and fluid energy mill grinding, satisfactory powders may be obtained by ball milling, hammer milling in inert atmosphere. While ball or pebble milling the cartilage with the extracting liquid gives satisfactory results, other methods, such as mixing the cartilage powders in the liquids with a high speed, high shear, closed turbine mixer or passing the extraction mixture through a pressure homogenizer, preferably at pressures in excess of 4000 p.s.i. will also give extracts of high activity.

EXAMPLE IV

Calf tracheal cartilage powder having a maximum particle size of 40 microns was mixed with about an equal part of anhydrous propylene glycol. This pre-mix was then added to "Neobase" (an ointment base made by Burroughs Wellcome & Co. of Tuckahoe, N.Y.), which contains the following ingredients:

Glyceryl monostearate
TWEEN-61 (polyoxyethylene sorbitan monostearate)
Span-60 (sorbitan monostearate)
Paroleine (liquid paraffin)
Propylene glycol
Methyl-para-hydroxy benzoate
Water (about 50 percent or more)
Diluted with about 50 percent additional water in an amount to yield a composition having about 10 percent of said powder.

Thus, an ointment formulation useful for the topical treatment of degenerative joint afflictions is formed, although it should be understood that other ointments and salves and salve bases may incorporate the powder or extract of the present invention.

As indicated previously, the cartilage extracts of this invention provide relief from the symptoms of degenerative joint afflictions, as evidenced by increased mobility and lessening or total disappearance of pain in the affected joints. The length of symptomatic remission varies, from patient to patient, depending upon the severity of the disease. In most cases, patients have remained asymptomatic for four months to a year. In some very severe cases, the symptoms returned after six weeks at which time the administration of a booster dose equivalent to a single daily dosage (i.e., injection of about 100 cc of sterile extract into two to four subcutaneous depots at one time) provided rapid relief.

As previously indicated, the cartilage product may also be applied topically in the area of the afflicted joint to provide symptomatic relief. In a clinical situation the cartilage ointment prepared in Example IV substantially stopped the symptoms in one moderate case of rheumatoid arthritis within several hours after application of the ointment. The topically applied ointment preparations contain cartilage powder having an average particle size no greater than about 150 microns. Optimum results are obtained when the average particle size is below about 70 microns, with the preferred range being about 15 to 45 microns. The efficacy of the topically applied ointment is improved if the affected area is first bathed in warm water for about 10 to 20 minutes. Thereafter, the ointment formulation is applied by mildly rubbing it into the skin around the affected area.

A group of 28 patients having osteoarthritic conditions (i.e., individuals with proven lesions by X-ray and with severe symptomatology in the usual joint distribution pattern) involving a representative cross-section of the joints subject to attack by this disease were treated by subcutaneous injection of the cartilage extracts according to this invention. In each instance the treatment was:

Administration of the total dose over a period of three to eight weeks by injecting 50 to 100 cc's of the extract every third day. The material was introduced into each individual by subcutaneous injection of a sterile 6% (ph6) iso-osmolar saline extract into two to four separated depots of 25 to 50 cc each. The injections were discontinued (even if the total dosage had not been reached) when the patient experienced a marked (i.e., protracted) relief from symptoms. The following tabulation of case reports demonstrate the results obtained with the cartilage extract injection therapy of this invention:

Case Report Definitions

Pain — described essentially in the patient's terminology

Functional Disability:
  Incapacitating — Patient unable to carry on normal activities and is confined to bed or chair except for infrequent and painful excursions of short length of time.
  Marked — Patient severely restricted in movements but able to carry on some outside activities at a slow pace and with much pain.
  Considerable — Patient able carry on normal activities but with constant pain and difficulties.
  Slight — Patient has no apparent diminution in capacity for most activities but is constantly aware of pain and of the need to avoid extremes of motion.

Results of Therapy: (Rating)
  Excellent — Virtually all pain and disability have disappeared leaving only slight discomfort if any.
  Good — Marked decrease in pain and greatly increased mobility of the affected joints. The patient reports some residual pain and disability.
  Fair — Good to excellent results achieved initially but remission short-lived (up to four weeks) after which considerable pain and disability returns.

EXTRACT INJECTION IN OSTEOARTHRITIS

| PATIENT | AGE | SEX | Joint Involvement | PAIN | Functional Disability | Cartilage powder extract Total Dose (cc) | Results of Therapy |
|---|---|---|---|---|---|---|---|
| I | 56 | F | Thoracic and lumbosacral spine Knees | Severe | Marked | 660 cc | Excellent |
| II | 62 | M | Lumbosacral joints, hips, knees | Severe | Incapacitating | 204 cc | No apparent effect. Has had one hip replaced |
| III | 68 | F | Entire spine, feet, ankles, knees, right rib cage | Severe | Marked | 500 cc | Good |
| IV | 68 | F | Cervical spine, acromio-clavicular joints | Severe | Marked | 160 cc | Excellent |
| V | 60 | F | Thoracolumbar spine | Severe | Considerable | 100 cc | Excellent |
| VI | 82 | F | Thoracolumbar spine, knees | Severe | Marked | 500 cc | Excellent |
| VII | 62 | F | Cervical spine, fingers, knees | Severe | Considerable | 450 cc | Excellent |
| VIII | 66 | F | Right humerus greater tuberosity, left hand | Severe | Considerable | 250 cc | Excellent |
| XX | 63 | M | Cervical, lower thoracic, lumbar and right lumbosacral spine | Severe | Marked | 550 cc | Excellent |
| XXI | 63 | F | Thoracic and lumbar spine, right hip | Moderate | Slight | 600 cc | Excellent |
| XXII | 72 | M | Thoracic and lumbar spine, right hip | Severe | Marked | 500 cc | Excellent |
| XXIII | 76 | M | Thoracic and lumbar spine osteoarthritis | Severe | Incapacitating | 1200 cc | Good |
| XXIV | 68 | M | Lumbosacral spine | Severe | Marked | 500 cc | Excellent |
| VIX | 75 | F | Entire spine, hands, knees | Severe | Considerable | 550 cc | Excellent |
| X | 74 | F | Thoracic and lumbar spine, hands | Severe | Considerable | 150 cc | Excellent |
| XI | 71 | M | Thoracic and lumbar spine | Severe | Considerable | 500 cc | Good |
| XII | 55 | F | Cervical spine, wrists | Severe | Considerable | 500 cc | Fair |
| XIII | 65 | F | Cervical spine | Severe | Considerable | 600 cc | Fair |
| XIV | 70 | M | Cervical spine | Severe | Considerable | 350 cc | Good |
| XV | 54 | M | cervical and lumbar spine, right hip | Severe | Incapacitating | 1000 cc | Excellent |
| XVI | 53 | F | Cervical and lumbosacral spine | Severe | Marked | 600 cc | Excellent |
| XVII | 55 | F | Cervical and lumbar spine | Severe | Marked | 650 cc | Excellent |
| XVIII | 43 | M | Cervical and lumbar spine | Moderate | slight | 500 cc | Excellent |
| XIX | 83 | F | Entire spine, hands, knees | Severe | Incapacitating | 700 cc | Good |

In none of the preceding cases was there any evidence of toxicity (either clinically or in a wide variety of laboratory tests) attributable to administration of the cartilage extracts of this invention. In many of the above cases a protracted symptomatic remission period was obtained with the instant invention after treatment by direct injection of corticosteroids into the afflicted joints had failed to provide relief for more than about a week.

It is also contemplated that the cartilage product may be employed in this invention in the form of a liquid suspension for administration by injection.

What is claimed is:

1. A method of treating degenerative joint afflictions to obtain a protracted symptomatic remission period, the alleviation of pain and the promotion of increased joint mobility in a human suffering from said degenerative joint affliction which comprises subcutaneously administering to said human in a distensible area of the body and in a plurality of individual treatments a total dose of between about 150 and 1,000 cc consisting essentially of a liquid extract of essentially pure granulated cartilage material, substantially free from adhering tissue, and subcutaneously administering to said human at least about 10 cc of said liquid extract in each of said individual treatments.

2. The method of claim 1 wherein each of said individual treatments comprises forming at least one subcutaneous depot in a distensible area of the body containing from about 10 cc to about 50 cc of said liquid cartilage extract.

3. The method of claim 2 which comprises administering said total dose at predetermined intervals over a period of from about 3 to about 8 weeks.

4. The method of claim 2 wherein each of said subcutaneous depots contains about 25 cc of said liquid cartilage extract.

* * * * *